US012760255B2

(12) United States Patent
Kiraz et al.

(10) Patent No.: US 12,760,255 B2
(45) Date of Patent: Oct. 13, 2026

(54) MICROFLUIDIC PLATFORM FOR ENABLING CELL CULTURING IN A THREE DIMENSIONAL MICROENVIRONMENT

(71) Applicants: KOC UNIVERSITESI, Istanbul (TR); ISTANBUL TEKNIK UNIVERSITESI, Istanbul (TR)

(72) Inventors: Alper Kiraz, Istanbul (TR); Kemal Baysal, Istanbul (TR); Ahmet C Erten, Istanbul (TR); Berna Morova, Istanbul (TR); Ateeq Ur Rehman, Istanbul (TR); Umut Can Coskun, Istanbul (TR)

(73) Assignees: KOC UNIVERSITESI, Istanbul (TR); ISTANBUL TEKNIK UNIVERSITESI, Istanbul (TR)

( * ) Notice: Subject to any disclaimer, the term of this patent is extended or adjusted under 35 U.S.C. 154(b) by 1266 days.

(21) Appl. No.: 17/623,265

(22) PCT Filed: Jun. 17, 2020

(86) PCT No.: PCT/TR2020/050520
§ 371 (c)(1),
(2) Date: Dec. 28, 2021

(87) PCT Pub. No.: WO2020/263206
PCT Pub. Date: Dec. 30, 2020

(65) Prior Publication Data
US 2022/0364029 A1 Nov. 17, 2022

(30) Foreign Application Priority Data
Jun. 28, 2019 (TR) ................................ 2019/09710

(51) Int. Cl.
*C12M 3/06* (2006.01)
*B01L 3/00* (2006.01)
*C12M 1/00* (2006.01)

(52) U.S. Cl.
CPC ....... *C12M 23/16* (2013.01); *B01L 3/502746* (2013.01); *C12M 23/34* (2013.01); (Continued)

(58) Field of Classification Search
CPC .............................. C12M 23/16; C12M 23/34
See application file for complete search history.

(56) References Cited

FOREIGN PATENT DOCUMENTS

CN 106566863 A 4/2017
KR 20180079917 A * 7/2018 ......... B81C 1/00714
(Continued)

OTHER PUBLICATIONS

English Translation of CN106566863A, Qin et al. (Year: 2017).*
(Continued)

*Primary Examiner* — Michael A Marcheschi
*Assistant Examiner* — Jonathan E Lepage
(74) *Attorney, Agent, or Firm* — Bayramoglu Law Offices LLC

(57) ABSTRACT

A three dimensional (3D) microfluidic cartridge suitable for reproduction of cells in the 3D microfluidic cartridge and for observing an angiogenesis process is provided. The 3D microfluidic cartridge includes a side area, wherein a height of the side area is greater than a height of central area. With the 3D microfluidic cartridge, a 3D cell culture is carried out, tumor spheroids are formed in the 3D microfluidic cartridge, and angiogenesis potentials of the tumor spheroids are measured. Further, responses of endothelial cells against angiogenic or antiangiogenic effects of various small molecules, drugs, and protein therapeutics are measured in the 3D microfluidic cartridge.

12 Claims, 5 Drawing Sheets

(52) U.S. Cl.
CPC .................. *B01L 2300/0867* (2013.01); *B01L 2300/0874* (2013.01); *C12N 2533/54* (2013.01)

(56) References Cited

FOREIGN PATENT DOCUMENTS

| | | | | | |
|---|---|---|---|---|---|
| WO | 2009126524 | A2 | | 10/2009 | |
| WO | WO-2014183118 | A1 | * | 11/2014 | ............ C12M 23/16 |
| WO | WO-2016076795 | A1 | * | 5/2016 | ............ C12M 23/24 |
| WO | 2019010587 | A1 | | 1/2019 | |
| WO | WO-2019046307 | A1 | * | 3/2019 | ........... G01N 33/575 |
| WO | WO-2020056320 | A2 | * | 3/2020 | ............ C12M 25/14 |

OTHER PUBLICATIONS

Lin Wang, et al., Chemical and physical modifications to poly(dimethylsiloxane) surfaces affect adhesion of Caco-2 cells, Journal of Biomedical Materials Research Part A, 2009, pp. 1260-1271.

* cited by examiner

MICROFLUIDIC PLATFORM FOR ENABLING CELL CULTURING IN A THREE DIMENSIONAL MICROENVIRONMENT

CROSS REFERENCE TO THE RELATED APPLICATIONS

This application is the national stage entry of International Application No. PCT/TR2020/050520, filed on Jun. 17, 2020, which is based upon and claims priority to Turkish Patent Application No. 2019/09710, filed on Jun. 28, 2019, the entire contents of which are incorporated herein by reference.

TECHNICAL FIELD

The present invention relates to a microfluidic platform suitable for reproduction of cells therein.

BACKGROUND

Angiogenesis is a physiological mechanism through which new blood vessels are formed from existing vessels. Inactive endothelial cells that do not reproduce are stimulated by growth factors, and formation of a new vessel from an existing vessel is encouraged by means of their activation, proliferation and migration (displacement). This mechanism is used by tumors to meet the increased oxygen and nutrient needs during the growth of tumors. One of the critical indicators that determine the capacity of a tumor to spread and malignancy is angiogenic potential of the tumor. Angiogenic potential is also associated with progression of the disease (prognosis) in certain types of tumors. There are several genetic tests for determining the angiogenic potential. However, these do not show actual angiogenic potentials of tumor cells accurately.

In an angiogenesis experiment, primer endothelial cells isolated from umbilical cord or micro-vessels are used. In the current state, angiogenic experiments are carried out in 2 dimensional (2D) cultures. 3 dimensional (3D) cultures mimic physiological properties and responses of cells better.

3D culture systems produced in micro scale allow the researchers to control the culture environment by means of strictly controlling the cell shape, dimensionality, adhesive surfaces/ligands, and amount of cell-cell contact, level and nature of soluble factors. Hydrogels manufactured from biocompatible macromolecules are used in order to create these 3D culture systems which provide cell binding and proliferation signals. The said macromolecules can be natural compounds such as collagen, fibrin or gelatin, as well as they can be synthetic compounds such as GelMA. Macromolecules that are preferred for hydrogels have suitable reagent groups for the electrostatic interaction of charged amino acid side groups present in proteins in cell membranes. Furthermore, these have to be transparent in order to allow cellular imaging with light and fluorescent microscopy. In the state of the art, various angiogenesis models in hydrogels are available.

International patent document no WO2009126524, an application known in the state of the art, discloses a 3D microfluidic platform in order to carry out angiogenesis process.

International patent document no WO2016076795, an application known in the state of the art, discloses a microfluidic platform in order to examine cell based interactions.

Micro scale pillars are used in culture dishes in the state of the art. In a microfluidic platform suitable for angiogenesis, it should be ensured that endothelial cells and tumor cells are located at a distance where they can be affected by each other. Furthermore, these cells should be provided to act according to the concentration gradients of the factors besides angiogenic factors, and avoid mixing with each other. Therefore, there is a need for an alternative cell culture platform suitable for the formation of angiogenesis in a 3D system and its visualization over time.

SUMMARY

The objective of the present invention is to provide a microfluidic platform which is suitable for adding macromolecules that can form hydrogel in liquid form therein.

Another objective of the present invention is to provide a microfluidic platform suitable for determining the angiogenic potential of cells obtained from a tumor.

Yet another objective of the present invention is to provide a microfluidic platform suitable for measuring angiogenic or antiangiogenic effects of small molecules, drugs and protein therapeutics that are developed.

BRIEF DESCRIPTION OF THE DRAWINGS

The microfluidic platform provided in order to achieve the objectives of the present invention is illustrated in the accompanying drawings, in which.

Figure 1:
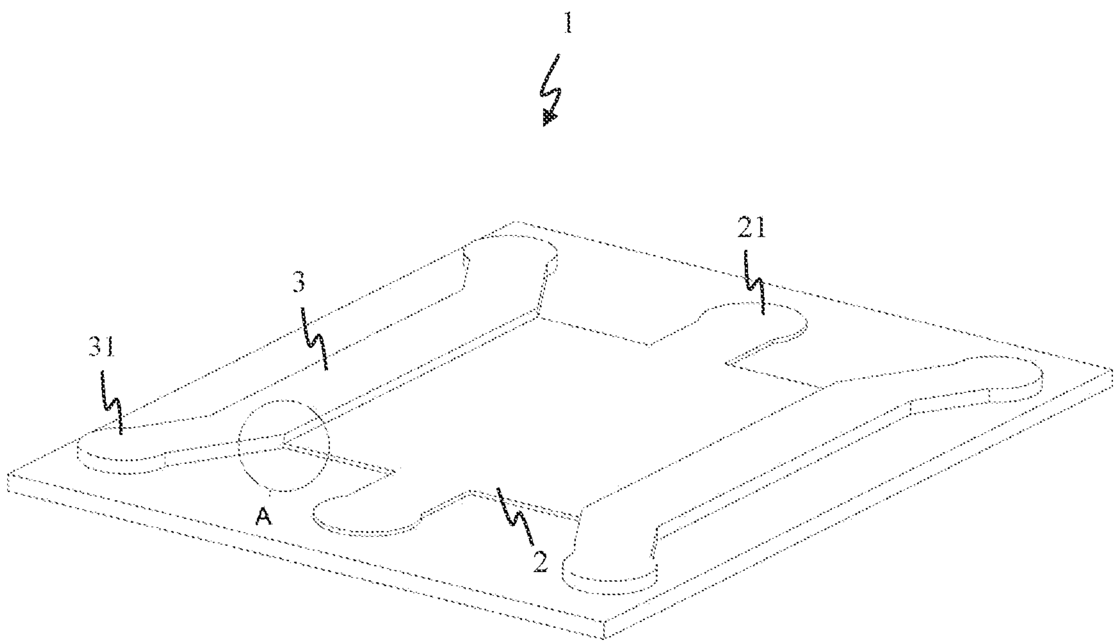
FIG. 1 is a view of an embodiment of microfluidic platform of the present invention.
Figure 2:
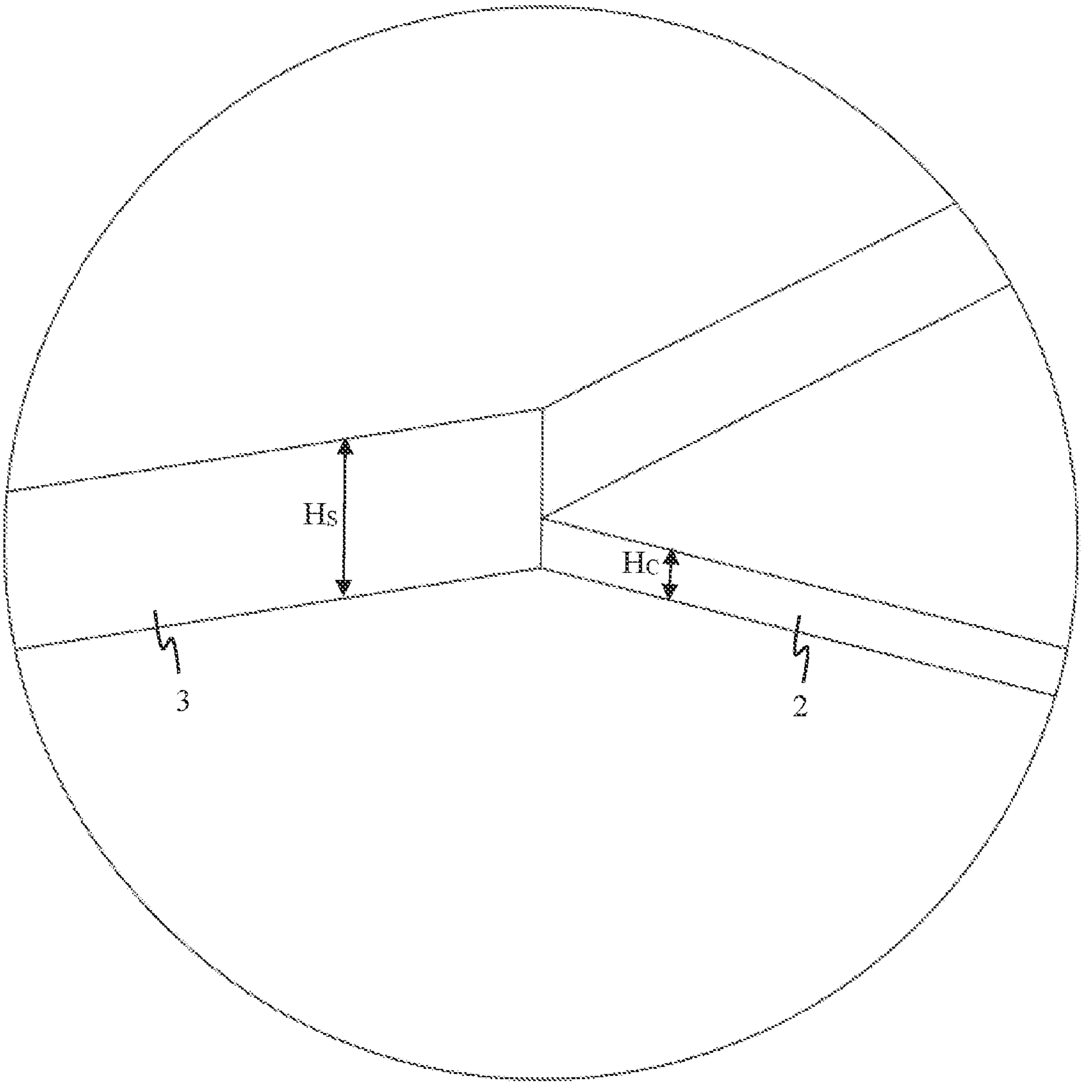
FIG. 2 is the view of detail A shown in FIG. 1.
Figure 3:
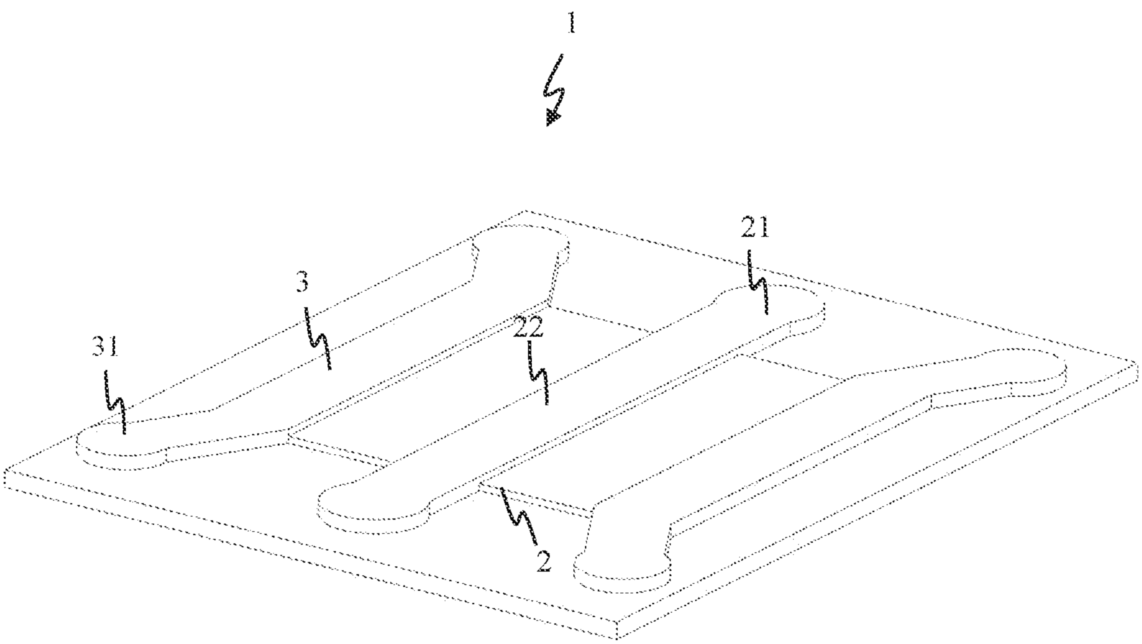
FIG. 3 is a view of another embodiment of microfluidic platform of the present invention.
Figure 4:
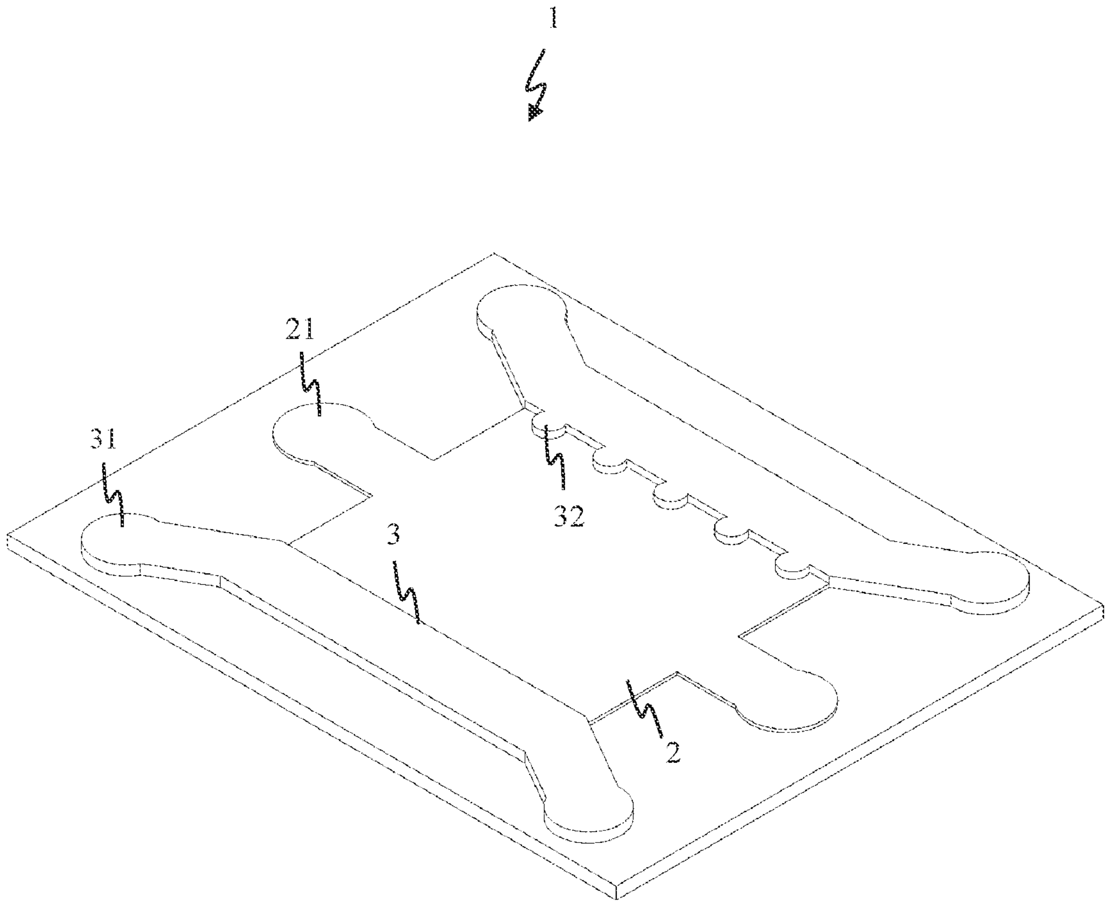
FIG. 4 is a view of yet another embodiment of microfluidic platform of the present invention.
Figure 5:
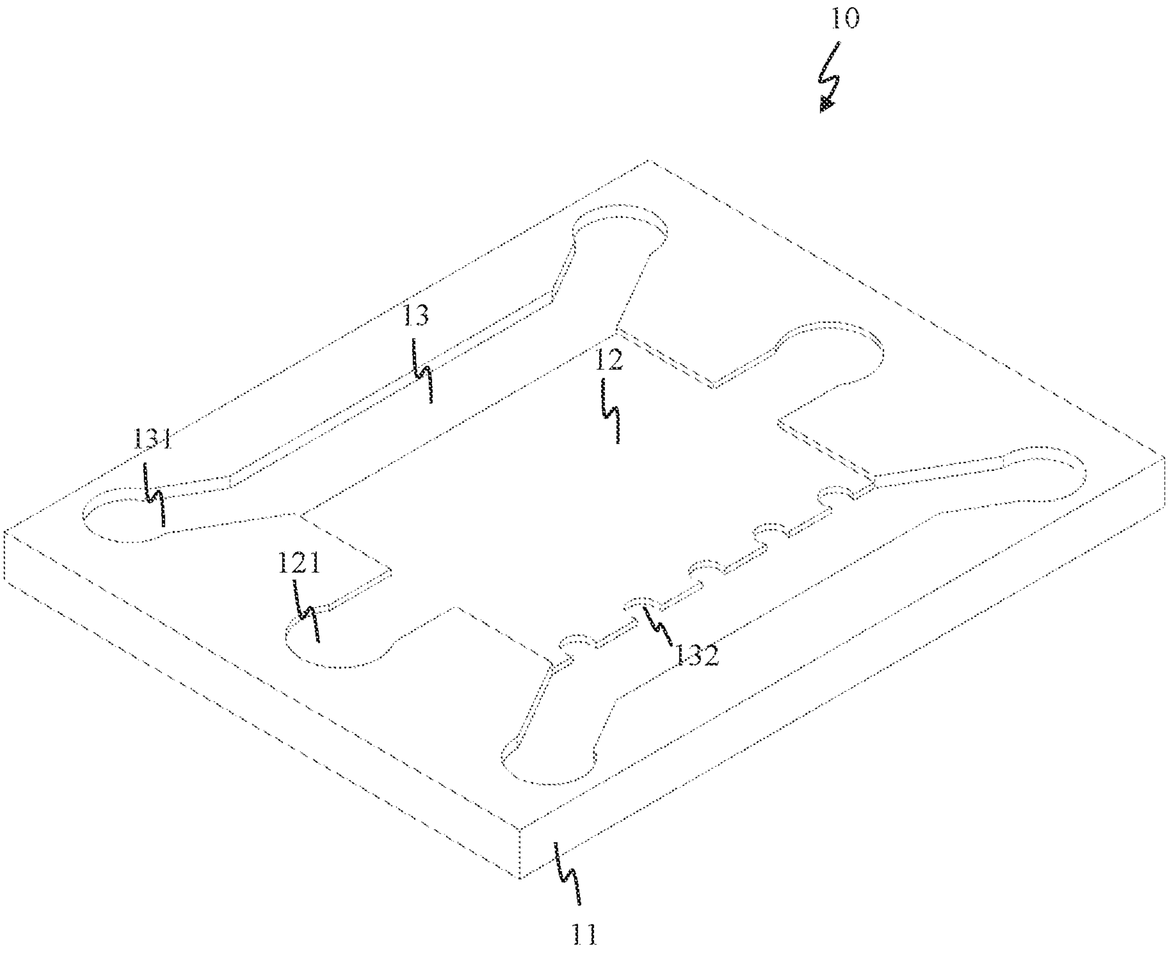
FIG. 5 is a view of a mold suitable for production of microfluidic platform of the present invention.

The components shown in the figures are each given reference numbers as follows:

1. Microfluidic platform
2. Central area
    - 21. Feeding channel
    - 22. Protrusion
3. Side area
    - 31. Feeding channel
    - 32. Pocket
10. Mold
11. Base
12. Central area protrusion
    - 121. Feeding channel protrusion
13. Side area protrusion
    - 131. Feeding channel protrusion
    - 132. Pocket protrusion

DETAILED DESCRIPTION OF THE EMBODIMENTS

The microfluidic platform (1) suitable for the reproduction of cells therein essentially comprises at least one central area (2) which is suitable for receiving a solution therein, comprises at least one feeding channel (21) for feeding the said solution, at least two side areas (3) which are provided mutually on opposite sides of the central area (2), each one of which has at least one feeding channel (31) for feeding material, the height of which is greater than the height of the central area (2).

The microfluidic platform (1) of the present invention which is suitable for reproduction of cells therein essentially comprises at least one central area (2) suitable for receiving a solution therein. The said solution is fed via at least one feeding channel (21) connected to the central area (2).

There are at least two opposite side areas (3) located mutually around the central area (2). The heights (Hs) of the said side areas (3) are greater than the height (Hc) of the central area (2). Each one of these side areas (3) have at least one feeding channel for feeding material to the said side areas (3). By means of the heights (Hs) of the edge areas (3) being greater than the height of the central area (2), the solution fed to the central area (2) reaches the side areas (3), and then ends its progress due to the surface tension and capillary effect when it meets the air therein. Therefore, the said solution does not overflow the side areas (3).

The solution to be fed to the central area (2) is preferably a solution containing one, several or all of the natural, biocompatible macromolecules such as collagen, fibrin or gelatin. However, the natural macromolecules that the said solution may contain are not limited to these. The solution may also contain at least one synthetic macromolecule such as GelMA alone or in combination with the natural macromolecules mentioned above. The said solution is transformed into a hydrogel by changing pH value and/or temperature of the said solution.

At least one type of cell is delivered to at least one of the side areas (3). The said cell is preferably delivered inside a medium such as DMEM (Dulbecco's Modified Eagle Media) to the side area (3) via the feeding channel (31). The said cells interact with the hydrogel in the central area and hold onto this. Tumor cells, mesenchymal stem cells and endothelial cells are among the cells that can be placed here. However, the cells that can be fed are not limited to these.

Different types of cells can be fed to each of the side areas (3). For example, tumor cells are fed to one side area (3), whereas endothelial cells can be fed to another side area (3).

In one embodiment of the invention, the central area (2) has at least one protrusion (22).

In one embodiment of the invention, at least one side area (3) comprises at least one pocket (32) suitable for the accumulation of at least one tumor cell therein. Tumor cells accumulate in the pocket (32), thereby forming a tumor spheroid. In this embodiment, the microfluidic platform (1) is positioned parallel to the ground plane in the beginning, and then the microfluidic platform (1) is rotated by the user such that it will be almost 90 degrees to the ground plane. In other words, when the side area (3) is rotated such that it will be almost perpendicular to the ground plane, the tumor cells proliferated in the side area (3) having the pocket (32) get into motion with the effect of gravitation and enter into the said pocket (32). Therefore, the said cells can be observed together. In a preferred embodiment of the invention, there is a plurality of pockets (32) on the side area (3) and the said pockets (32) allow multiple tumor spheroids to be tested simultaneously by means of the accumulation of multiple tumor cells therein.

In the preferred use of the microfluidic platform (1) of the present invention, the insides of the central area (2) and the side areas (3) are primarily filled with air. The user feeds a solution in the desired formulation to the central area (2) via the feeding channel (21). The said solution moves along the central area (2). However, when the said solution reaches the border of the side areas (3), it does not move further due to the surface tension and capillary effect. The user then transforms the solution into hydrogel by changing the pH and/or temperature of the solution. After this step, the cell or cells desired to be reproduced are fed to the side areas (3) via the feeding channel (32).

A mold (10), which is suitable for production of the microfluidic platform (1) of the present invention, essentially comprises at least one base (11), at least one central area protrusion (12) which is for forming the central area (2) of the microfluidic platform (1) on the said base (11), at least one feeding channel protrusion (121) which is for forming the feeding channel (21) connected to the central area (2), at least one side area protrusion (13) which is for forming the side areas (3), and at least one feeding channel protrusion (131) which is for forming the feeding channel (31) connected to the side area (3). The height of the side area protrusion (13) is greater than the height of the central area protrusion (12).

In one embodiment of the invention, at least one side area protrusion (13) has at least one pocket protrusion (132) in order to form the pocket (32) on the side area (3).

A production of the microfluidic platform (1) of the present invention is characterized by the steps of

- pouring polydimethylsloxane (PDMS) on the abovementioned mold (10),
- treating the poured material at a predetermined time period and temperature,
- removing the treated material from the mold,
- covering the removed material on another material coated with poly-D-lysine (PDL)
- treating the central area (2) with PDL.

Another production method of the microfluidic platform of the present invention, its production can be realized from various polymers by means of using hot pressing (embossing) or injection molding.

Three dimensional (3D) cell culture can be carried out with the microfluidic cartridges (microfluidic platforms) present in this invention. Tumor spheroids can be formed in the cartridges and the angiogenesis potentials of these spheroids can be measured. In addition to this, the responses of endothelial cells to angiogenic or antiangiogenic effects of various small molecules, drugs, and protein therapeutics against can be measured in the microfluidic platform of the present invention. Endothelial and/or tumor cells added to the microfluidic platform can be cultured and their interactions can be examined by means of microscopic imaging methods.

What is claimed is:

1. A microfluidic platform for reproduction of cells in the microfluidic platform, comprising

- at least one central area for receiving a solution in the at least one central area, wherein the at least one central area comprises at least one first feeding channel for feeding the solution,
- at least two side areas provided mutually on opposite sides of the at least one central area, each one of the at least two side areas has at least one second feeding channel for feeding a material, wherein
- one of the at least two side areas comprises three or more pockets suitable for accumulation of tumor cells and reproduction of tumor spheroids,
- a height of one side area of the at least two side areas is greater than a height of the at least one central area,
- the insides of the at least one central area and the at least two side areas are primarily filled with air such that a solution fed into the at least one central area reaches the at least two side areas, and then ends its progress due to the surface tension and capillary effect when it meets air therein, and therefore does not overflow the at least two side areas; and the at least one central area is treated with poly-D-lysine (PDL).

2. The microfluidic platform according to claim 1, wherein the at least one central area has at least one protrusion.

3. The microfluidic platform according to claim 1, wherein the at least one central area has the solution containing one, several, or all of natural, biocompatible macromolecules, wherein the natural, biocompatible macromolecules are collagen, fibrin or gelatin.

4. The microfluidic platform according to claim 1, wherein the at least one central area has the solution containing at least one synthetic macromolecule.

5. The microfluidic platform according to claim 1, wherein the microfluidic platform is produced with a hot pressing or an injection molding method.

6. The microfluidic platform according to claim 2, wherein the at least one central area has the solution containing at least one synthetic macromolecule.

7. The microfluidic platform according to claim 3, wherein the at least one central area has the solution containing at least one synthetic macromolecule.

8. The microfluidic platform according to claim 2, wherein the microfluidic platform is produced with a hot pressing or an injection molding method.

9. A mold suitable for a production of the microfluidic platform according to claim 1, comprising at least one base, at least one central area protrusion for forming the at least one central area of the microfluidic platform on the at least one base, at least one first feeding channel protrusion for forming the at least one first feeding channel connected to the at least one central area, at least one side area protrusion for forming the at least two side areas, and at least one second feeding channel protrusion for forming the at least one second feeding channel connected to one of the at least two side areas wherein one of the at least two side areas comprises three or more pockets for reproduction of tumor spheroids, and the at least one side area protrusion has three or more pocket protrusions for forming the three or more pockets on the one of the at least two side areas.

10. A production method for producing the microfluidic platform according to claim 1, comprising the following steps of:

pouring polydimethylsiloxane (PDMS) on a mold to obtain a poured material, wherein the mold comprises at least one base, at least one central area protrusion for forming the at least one central area of the microfluidic platform on the at least one base, at least one first feeding channel protrusion for forming the at least one first feeding channel connected to the at least one central area, at least one side area protrusion for forming the at least two side areas, and at least one second feeding channel protrusion for forming the at least one second feeding channel connected to one of the at least two side areas, treating the poured material at a predetermined time period and temperature to obtain a treated material, removing the treated material from the mold to obtain a removed material, covering the removed material with another material coated with poly-D-lysine (PDL), treating the at least one central area with the PDL.

11. The production method according to claim 10, wherein the at least one central area wherein the solution contains one, several, or all of natural, biocompatible macromolecules, wherein the natural, biocompatible macromolecules are collagen, fibrin or gelatin.

12. The production method according to claim 10, wherein the at least one central area wherein the solution contains at least one synthetic macromolecule.

* * * * *